United States Patent [19]

Hurst

[11] 4,113,565
[45] Sep. 12, 1978

[54] GLUCOSE ISOMERIZATION WITH IRON ION-THIOL ACTIVATOR ION-GLUCOSE ISOMERASE SYSTEMS

[75] Inventor: Thomas L. Hurst, Decatur, Ill.

[73] Assignee: A. E. Staley Manufacturing Company, Decatur, Ill.

[21] Appl. No.: 750,332

[22] Filed: Dec. 13, 1976

Related U.S. Application Data

[63] Continuation-in-part of Ser. No. 560,658, Mar. 20, 1975, Pat. No. 4,026,764.

[51] Int. Cl.$^2$ .............................................. C12D 13/02
[52] U.S. Cl. ................................. 195/31 F; 195/114
[58] Field of Search .................. 195/31 F, 62, 66 R, 195/114

[56] References Cited

U.S. PATENT DOCUMENTS

| 3,623,953 | 11/1971 | Cotter et al. | 195/31 F |
|---|---|---|---|
| 3,956,066 | 5/1976 | Coker et al. | 195/31 F |
| 3,974,036 | 8/1976 | Snell | 195/65 |
| 3,979,261 | 9/1976 | Outtrup | 195/31 F |
| 4,008,124 | 2/1977 | Fujita et al. | 195/31 F |
| 4,026,764 | 5/1977 | Hurst | 195/31 F |

OTHER PUBLICATIONS

Tz-Yuan et al., "D-Xylose Isomerase of Streptomyces griseus," Acta Biochimica et Biophysica Sinca", vol. 14, No. 3, pp. 342-350 (1964).
Perry et al., Chemical Engineer's Handbook, 4th ed., McGraw-Hill Book Co., New York, (1963) pp. 23-27.

Primary Examiner—Raymond N. Jones
Assistant Examiner—Thomas G. Wiseman
Attorney, Agent, or Firm—M. Paul Hendrickson; Charles J. Meyerson

[57] ABSTRACT

Iron ions may be effectively used as a metal activator or co-metal activator in glucose isomerization when used in conjunction with thiol activators. The thiol activators are characterized as being able to cleave disulfide linkages and include reducing reagents such as water-soluble $SO_3^=$ producing metal salts, ascorbic acid, thiocyanates, thioglycollates, etc. The thiol activator-iron ion activating system is especially effective when used in conjunction with at least one other metal ion activator such as magnesium, manganese or cobalt ions. Effective enzymatic glucose isomerization, without using cobalt ions, is achievable by a magnesium-iron-thiol activator-isomerase system.

16 Claims, No Drawings

GLUCOSE ISOMERIZATION WITH IRON ION-THIOL ACTIVATOR ION-GLUCOSE ISOMERASE SYSTEMS

This application is a continuation-in-part of U.S. application Ser. No. 560,658 filed Mar. 20, 1975, now U.S. Pat. No. 4,026,764.

BACKGROUND OF THE INVENTION

It is well known that certain enzymes isomerize aqueous aldose monosaccharides to ketose monosaccharides and vice versa. Within recent years, isomerases have attracted considerable commercial interest in glucose syrup isomerization reactions. Such enzymes are frequently referred to by the trade as glucose isomerases.

A typical commercial glucose isomerization process results in an isomerized glucose syrup product containing approximately 40–50% fructose and 50–60% glucose. The glucose isomerization process normally requires from about 24 to 72 hours and will be conducted at temperatures above 50° C. (usually between 60° to 70° C.). Achieving and maintaining sufficient isomerase activity throughout the isomerization process is necessary to obtain acceptable fructose yields.

Isomerases are inherently susceptible to deactivation. In batch processes, reduced isomerase activity is normaly compensated by charging the reactor with sufficient isomerase to complete the isomerization reaction. In a continuous ismerization process, isomerase deactivation may be partially corrected by periodic addition of fresh isomerase. Isomerase deactivation creates difficulties and additional expense in the manufacture of fructose syrups.

Illustrative reported glucose isomerases include those derived from organisms of the Acetobacter genus, (e.g., A. Aceti IFO 3282, *A. rubiginosus* IFO 3243, *A. suboxydans* NRRL B 72); Aerobacter genus, (e.g., A. strain HN-56, *A. cloacae* KN-69, *A. cloacae* NRC 491 and NRC 492); *B. stearothermophilus* genus (e.g., ATCC 31265, NRRL B-3680, NRRL B-3681 and NRRL B-3682); Bacillus genus (e.g., *B. coagulans* HN-68, NRRL B-5350 and NRRL B-5351, *B. megaterium* ATCC 15450, *B. fructosus* ATCC 15451, etc.); Arthrobacter genus (e.g., A. Sp. IFO 3576, 3580, 3585, 3591, 3601, 3604, *A. nov. sp.* NRRL B-3724, 3725, 3727 and 3728); Brevibacterium genus (e.g., *B. pentoso-aminoacidicum, B. Lipolyticum* IFO 3633); *Coryne bacterium* (Sp. IFO 3597, IFO 3606, IFO 3618, IFO 3697); *Escherichia intermedia* HN-500; Lactobacillus genus (e.g., *L. brevis, L. fermenti, L. gayoni, L. mannitopoeus, L. pentoaceticus*); *Leuconostoc mesenteroides;* Micrococcus genus (e.g., M. rubens ATCC 186, M. varians ATCC 399); *Mycobacterium* sp IFO 3603 and IFO 3611; *Mycoccocus* Sp. IFO 3583; Pseudomonas genus (e.g., *P. fluorescens, P. boreopolis, P. coronafaciens, P. striafaciens, P. syncyanea, P. synxantha, P tabaci*); Nocardie genus (e.g., *N. asteroides, N. dassonvillei); Micromonospora coerulea; Microbispora rosea; Microellobosporia flavea; Serratia plymuthica;* Streptomycetes genus (e.g., S. sp ATCC 21175, 21176, *S. achromogenes, S. albus* YT-4, S. albus YT-51, *S. aureus, S. bobiliae, S. marcesens, S. californicus, S. coelicolor, S. diastaticus, S. echinatus, S. flavovirens, S. fradiae, S. fulvissimus, S. galilaeus, S. gedamemsis, S. griseolus, S. horbaricolor, S. hydroscopicus, S. lipmanii, S. niveoruber, S. olivaceus* NRRL B-3583, *S. olivochromogenes* ATCC 21114, *S. phaeochromogenes, S. rochei, S. roseochromogenes, S. rutgerensis, S. tendae, S. venaceus, S. venezuelae* ATCC 21113, *S. virginiae, S. viridochromogenes, S. wedmorensis,* etc.); Actinoplanes genus (e.g., *A missouriensis, A. philippinensis, A. armeniacus*); etc.

Continuous fixed-bed reactors are primarily employed to produce fructose syrups. In continuous reactors, the desired fructose level is typically obtained by permitting a high glucose containing syrup to flow through a bed of immobilized glucose isomerase or a series of reactor beds until the desired fructose yield is achieved. Fructose productivity by a fixed bed reactor is directly proportional to the isomerase activity. Decreased yields inherently arise because the isomerase deactivates. Ultimately the isomerase deteriorates and becomes totally ineffective and requires recharging with fresh isomerase.

It is well known that isomerases are less susceptible to deactivation when the isomerization reaction is conducted in the presence of one or more metal ion activators. Such activators stabilize and activate the isomerase. It is conventional to incorporate these metal activators into the dextrose feed syrup. The metal ion activators and the requirements will vary and depend upon the isomerase type. When an isomerase is isolated from a new source or in a different form, it is conventional to establish its metal ion activator requirements. Suppliers of commercial isomerases customarily provide technical information with respect to its metal ion activator requirements for a glucose isomerization process.

The activating and stabilizing effect of cobalt, magnesium and manganese upon isomerases in the isomerization reaction of dextrose to fructose have been extensively reported by numerous researchers (e.g., see Tsumura et al., Agr. Biol. Chem., Vol. 29, No. 12, p. 1129–1134, 1965; Yamanaka, Agr. Biol. Chem., Vol. 27, No. 4, p. 265–270, 1963: Takasaki et al., Agr. Biol. Chem., Vol. 33, No. 11, p. 1527–1534, 1969; S. Yoshimura et al., Agr. Biol. Chem., Vol. 30, No. 10, p. 1015–1023, 1966; Danno et al., Vol. 31, No. 3, p. 284–292, 1969; Natake et al., Agr. Biol. Chem. Vol. 28, No. 8, p. 510–516, 1964; Tz-Yuan et al., Sheng Hua Hsuah Pao 4, (3), p. 342–350, 1964; Tsumura et al., Vol. 29, No. 12, p. 1123–1128, 1965; Sato, Dempunto Gijutsu Kenkyu Kaiho, No. 32, p. 81–88, 1965; Fratzke, National Science Foundation Report No. NS-RA-T-74-099, 1974). Cobalt ions in combination with either magnesium or manganese ions are reportedly very effective stabilizers and activators for most glucose isomerases. Calcium and nickel ions in combination with either manganese or magnesium ions have been proposed as isomerase activators (e.g., see Japanese Patent Appln. NS 112591/76). The use and safety of cobalt ions in the production of food grade products is dubious. The growth promoting effects of iron in the culturing of organisms and isomerase production has been recognized. Most studies pertaining to the effect of iron ions upon isomerase activity tend to show it is generally ineffective, especially when compared to either cobalt, manganese or magnesium ions and combinations thereof. An alternative means for producing food grade fructose without necessitating cobaltous ions and yet provide an acceptable level of fructose productivity and isomerase stability would be a desirable goal.

It has reported that certain isomerases are activated by conducting the isomerization reaction in the presence of thiol activating reagents such as glutathione and cysteine (e.g., see J. Agri. Chem. Soc., Japan 36, No. 12, p. 1013–1016, 1962 by Y. Takasaki et al.; J. Biol. Chem. 218, p. 535, 1956, by M. J. Palleroni et al.; J. Am. Chem.

Soc. 77, p. 1663, 1955 by M. W. Slein; and Agr. Biol. Chem., Vol. 28, No. 8, p. 510–516, 1964 by M. Natake et al.). Researchers have also reported sulfhydryl binding agents which react with sulfhydryl groups (e.g., cuprous ions such as cuprous sulphate or chloride, p-chloro-mercuribenzoate, monoiodoacetate, mercurous ions, zinc sulphate, etc.) will inhibit or destroy glucose isomerase activity. Conducting the isomerization reactions in the presence of oxidizing agents, including nascent oxygen, reportedly have an inhibitory effect upon glucose isomerase activity.

OBJECTS

It is an object of the present invention to provide a means for using iron ions as an effective metal activator in enzymatic glucose isomerization reactions.

An additional object of the present invention is to provide an acceptable level of enzymatic conversion to fructose without requiring the addition of cobalt ions to a dextrose feed syrup.

Another object of the invention is to isomerize glucose to fructose with a glucose isomerase activating system which relies upon magnesium ions, iron ions and thiol activators.

A further object of the invention is to provide a method for enzymatically producing fructose syrups without necessitating extensive refining to remove cobalt ion impurities from a fructose syrup.

A still further object is to provide a method for enzymatically isomerizing dextrose to fructose and achieving a higher order of glucose isomerase activity than would be normally obtained with an activating system which relies upon magnesium ions and/or on iron ions.

A further object is to activate a dry isomerase preparation and obtain an activated isomerase which possesses greater effectiveness in a monosaccharide isomerization process.

Another object of this invention is to increase the half-life of an isomerase preparation in a monosaccharide isomerization process.

DESCRIPTION OF THE INVENTION

According to the present invention there is provided an improved method for isomerizing dextrose to fructose in the presence of metal ion activators or co-metal ion activator combinations, wherein the metal activators or co-metal ion activators stabilize and activate the glucose isomerase in a glucose isomerization reaction, the improvement which comprises isomerizing dextrose to fructose with glucose isomerase in the presence of water-soluble iron ions and water-soluble thiol activator ions.

The present invention provides an effective method for employing iron ions as a metal activator in glucose isomerization reactions. Ineffectiveness of iron ions in the isomerization reaction is overcome by an activating system comprised of iron ions and thiol activator in an amount sufficient to measurably increase the activity of the glucose isomerase. The thiol and iron system functions as an activator and stabilizer for glucose isomerases in the absence of other metal activators. Reasons why the thiol activators transform iron ions into an effective metal activator are not known. It is believed, however, that the thiol activator facilitates the formation and loading of the isomerase's active sites with the complexing iron activator in its most suitable molecular configuration.

The thiol activator-iron ion activating system generally applies to glucose isomerases and particularly those glucose isomerases known to be activated and stabilized by metal activator ions or co-metal activator ions selected from the group of water-soluble metal ions having an Atomic Number from 22 to 28 inclusive (e.g., see Periodic Table, Period 4, Series 4) and magnesium. The invention is advantageously applied to isomerases which are activated and stabilized by at least one metal activator selected from the group consisting of metal ions having an Atomic Number of 25 to 27 inclusive and magnesium. The thiol activator-iron ion system is preferably employed in conjunction with those glucose isomerases which characteristically have a higher glucose isomerase activity when the isomerization reaction is conducted in the presence of a combination of at least two metal activators selected from the group consisting of cobalt ions, manganese ions and magnesium ions in comparison to isomerization reactions wherein only one metal activator of the combination is used to isomerize the glucose to fructose. Glucose isomerases which possess a higher degree of glucose isomerase activity when the isomerization reaction is conducted in the presence of optimum catalytic amounts of cobalt ions and magnesium ions as opposed to when magnesium is used as the sole metal activator are most preferred. The invention especially applies to isomerases derived from organisms of the Streptomyces or Bacillus genus.

Water-insoluble or water-soluble glucose isomerases may be used. Since immobilized glucose isomerases are know to be more stable against enzymatic deterioration and generally possess a significantly longer half-life than water-soluble or unbound glucose isomerases, immobilized glucose isomerases are preferably used. Conventional, immobilized glucose isomerases (e.g., see cited articles and patents) are useful for this purpose.

Iron ions are essential to activate the glucose isomerase. Either ferrous ions or ferric ions or mixtures thereof may be used for this purpose. Suitable iron ion sources include the water-soluble, organic and inorganic acid salts of ferric or ferrous compounds. Illustrative ferrous or ferric salts include the iron salts of acetate, ammonium chlorides, ammonium sulfate, ammonium oxalates, hyposulfite, manganese chloride and citrate, sulfate, magnesium citrate, magnesium lactate, magnesium sulfate, sulfite, thiocyanate, tartrate, chloride, mixtures thereof and the like. Iron salts containing magnesium and/or thiol activator ions may be used to perform dual activating functions.

The iron ion requirements for the activity system herein will depend upon the character and composition of the isomerase, the type of isomerization process used (e.g., batch or continuous), whether or not the isomerase has been pretreated (e.g., see parent application Ser. No. 560,658 filed Mar. 20, 1975). Advantageously, the amount of iron present in the isomerization reaction in conjunction with the thiol activator should be sufficient to provide a measurable increase in the glucose isomerase activity over that which is achieved when magnesium is used as a sole activator for the isomerase (i.e., without iron activator ions). Illustrative iron ion concentrations used to activate the glucose isomerase may range from minute amounts (e.g., 1 part/million or $2 \times 10^{-5}$M) to about 1M or higher. In batch operations, iron levels in excess of about 1.3M do not appear to adversely affect glucose isomerase activity, but can lead to refining difficulties. It is desirable in a continuous operation to replenish or continuously provide the isomerase's active site with a sufficient amount of iron ions (and other co-metal activators if used) to compensate for iron ion or co-metal activator losses which inherently arise as a result of prolonged usage of the isomerase in a continuous isomerization process (e.g., by leaching, etc.) This maintains the glucose isomerase at a sufficiently high activity and stability level to effectively isomerize the dextrose to fructose. Typical iron levels for a continuous operation range from about $1 \times 10^{-5}$M to about 0.01M (preferably from about $5 \times 10^{-5}$M to about 0.001M) with batch operations being generally conducted at about $5 \times 10^{-4}$M to about 0.2M (preferably between about 0.001M to about 0.003M). For continuous operations wherein the iron ions are used in conjunction with at least one other co-metal activator ion (e.g., magnesium), an iron ion concentration of $7 \times 10^{-5}$M or higher is generally most suitable. Appropriate balance between iron ions and such other metal activators should be maintained during the isomerization reaction to achieve maximum fructose productivity. Excesses of either one of the metal co-activators over the other may result in a disproportionate displacement of the depleted co-metal activator from the glucose isomerase-metal complex.

In addition to the iron ions, the isomerase activator system relies upon a thiol activator. The reason why thiol activators, as a class, will measurably increase the activity of the isomerase-iron complex is not understood, especially since certain analysts have reported the absence of thiol bearing amino acids in isomerase for which these thiol activators have been found to be effective. Most typically the thiol activator will enhance the isomerase activity of the iron-isomerase complex by at least 5% and most typically by at least 10%.

Thiol activators which cleave disulfide linkages in equilibrium may be illustrated by the following reaction:

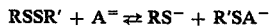

wherein R and R in the RSSR' represent organo groups (e.g., including protein molecules) joined together by a disulfide linkage, and $A^=$ represents reducing agent. Such reducing agents are representative thiol activators. Chemical reagents which are precursors or form $SO_3^=$ in aqueous solutions are particularly effective thiol activators. Such sulfite precursors include sulfur dioxide and water-soluble salts of sulfurous acid. Illustrative water-soluble salts of sulfurous acid include the alkaline metal sulfites (e.g., potassium or sodium salts of sulfite, bisulfite, pyrosulfite; lithium sulfite, etc.), water-soluble salts of metal activators which form $SO_3^=$ anions (e.g., the sulfites, bisulfites, hyposulfites, of ferrous, ferric, cobaltous, nickel, magnesium, etc.) and other water-soluble $SO_3^=$ producing salts of cations (e.g., ammonium sulfite, bisulfite, etc.), mixtures thereof and the like. Metal salts known to deactivate or inhibit glucose isomerase activity should be avoided (e.g., zinc, cupric, aluminum salts, etc.). Thiol activators which do not form sulfite ions, but function as reducing agents, include ascorbic acid, isoascorbic acid, water-soluble thiocyanate salts (e.g., thiocyanates of lithium, potassium, sodium, ammonium, cobaltous, magnesium, manganous, ferric, ferrous), cystein, mercaptoethanol, thioglycollate, (ethylene glycol) bis-thioglycollate, etc., mixtures thereof and the like.

The thiol activator should be provided to the glucose isomerase in an amount sufficient to increase the activating affect of the iron ion. Although the thiol activator requirements may be provided to the isomerase on a discontinuous or intermittent basis, it is advantageous to supply the isomerase with its thiol activator and iron ion requirements as dextrose feed syrup additives. Relatively small amounts of thiol activator (e.g., about 0.0001M in combination with the iron ions will generally result in increased glucose isomerase activity. Incremental increases in the thiol activator tend to proportionally increase isomerase activity of the system until a glucose isomerase activity plateau is reached, after which, the addition of more thiol activator does not appear to alter its activity level. Thiol activator concentrations well in excess of the level needed to achieve an equilibrated iron ion-isomerase complex are non-essential to the over-all isomerization reaction, but may be used to maintain an equilibrated system and inhibit the formation of undesirable by-products (e.g., malliard reaction products). For most isomerization reactions, effective isomerase activation will usually be achieved at thiol activator concentrations ranging from about 0.0002M to about 0.5M. Somewhat higher thiol activator ranges are advantageously used in batch operations (e.g., about 0.005M to about 0.2M) as opposed to continuous operations which are advantageously operated at a thiol activator concentration ranging from about 0.0003M to about 0.1M. Thiol activator concentrations from about 0.0004M to about 0.05M have been found to be particularly effective.

Although the iron-thiol activator system will activate and stabilize the glucose isomerase in glucose isomerization reactions, the iron-thiol activator system is generally more effective when combined with at least one other known activator for the isomerase (i.e., co-metal activator). In general, these other co-metal activators include magnesium and valance two metal ions having an Atomic Number ranging from 22 to 28 (e.g., see Period 4, Series 4 of the Periodic Table) and especially those of an Atomic Number of 25 to 27 (e.g., $Mn^{++}$ and $Co^{++}$), mixtures thereof and the like. The invention provides greater latitude as to potential metal activators for glucose isomerizations. This permits one to conduct the isomerization reaction with different or diverse metal activator combinations without destroying the efficacy of the isomerase. This ability to interchange or use different co-metal activators is particularly useful in isomerization processes wherein it is desired to substitute one metal for another because of processing or safety constraints.

In a more limited aspect of the invention there is provided a method for isomerizing dextrose to fructose with a glucose isomerase wherein the glucose isomerase is characterized as having a greater capacity to isomerize dextrose to fructose in the presence of $Mg^{++}$ and $Co^{++}$ ions in comparison to a isomerization reaction which is conducted in the presence of magnesium ion without cobaltous ions, the improvement which comprises isomerizing dextrose to fructose with said glucose isomerase in the presence of magnesium ions, iron ions and water-soluble thiol activator.

The combination of magnesium ions, iron ions and thiol activator activates and stabilizes the glucose isomerase. This activator and stabilizer system may be effectively conducted without adding cobalt to the isomerization media or dextrose feed syrup. The isomerization reaction may be effectively conducted by simply providing or adding the magnesium ion, iron ions and thiol activator to the dextrose solution (e.g., prior to or during the isomerization reaction) in an amount sufficient to maintain the glucose isomerase activity at a level greater than that obtained if magnesium ions were used as the sole metal ion activator (i.e., without the thiol activator and iron ion). In general, the magnesium-iron-thiol combination will not activate the glucose isomerase to as high a level as a magnesium-cobalt-thiol activator system, but the glucose isomerase activity will be significantly higher than most other co-metal activator systems which are conducted essentially without cobalt. This permits the fructose syrup manufacturer to achieve an acceptable fructose yield level without relying upon cobalt ions as a co-metal activator. The activating system achieves and maintains the glucose isomerase at a sufficiently high activity level for commercial use. Syrup cobalt contamination, as well as extensive refining and testing constraints so as to assure a fructose syrup quality fit for human consumption may be avoided by its use in an isomerization media essentially free from cobaltous ions.

The magnesium ions are most conveniently provided to the isomerase by dissolving a water-soluble salt of magnesium (e.g., magnesium chloride, magnesium oxalate, magnesium sulfate, magnesium carbonate, magnesium arsenate, magnesium ammonium arsenate, magnesium ammonium chloride, magnesium phosphate, magnesium sulfite, magnesium bicarbonate, magnesium citrate, magnesium hyposulfite, etc.) into a dextrose feed syrup. The optimum activator level for the magnesium ion will vary somewhat depending upon its character, source and form of the glucose isomerase. Due to the activating affect of the thiol activator-iron ion combination, magnesium ion concentrations below the optimum level conventionally employed in glucose isomerizations may be used. The magnesium ion concentrations herein, however, are advantageously within those amounts typically used to activate and stabilize glucose isomerases in conventional glucose isomerization reactions which rely upon magnesium ions as a co-metal activator and stabilizer. Illustrative magnesium ion concentrations range from about 0.0005M to about 0.3M. Advantageously used are magnesium ion concentrations of about 0.001M to about 0.1M and preferably in an amount ranging from about 0.002M to about 0.02M.

The magnesium-iron-thiol activating system is particularly adapted for those isomerases which are activated or require magnesium ions as a metal activator or co-metal activator and especially those isomerases which characteristically possess a higher state of activity when the isomerization reaction is conducted in the presence of both magnesium and cobalt ions versus an activator system wherein either the magnesium or cobalt is used separately to activate the isomerase (e.g., see Tsumura et al., 1965, Takasaki et al., 1969, Sato, 1965, Danno et al., 1967, Fratzke, 1974, etc. articles cited above). The cumulative activating effect of the magnesium-iron-thiol system is significantly higher than that achieved by magnesium alone or its combination with iron ions. Fructose yields of about 50–75% of those obtained with a magnesium-cobalt-thiol activator system are easily achieved with the magnesium-iron-thiol system.

Upon continued use a glucose isomerase will deteriorate and lose activity. The glucose isomerase deactivation is both permanent (i.e., irrepairable) and restorable. Permanent isomerase deactivation apparently arises from molecular and chemical transformation which occurs at the isomerase's activity sites. The restorable deactivating effect appears to arise from leaching of metal activator ions and reconfiguratons of the glucose isomerase molecule. The thiol activator and iron ion system (preferably in combination with other co-metal activators) preserves the efficacy of the active site and inhibits (e.g., stabilizes) the glucose isomerase from premature or permanent deactivation. Viability of the active sites are maintained or restored by making the thiol and iron ions available to the isomerase. Although it is possible to achieve restoration of the glucose isomerase to a more active state by intermittent charging of thiol activator-magnesium ions-iron ions to the isomerization reaction site, conservation and maintenance of peak glucose isomerase activity is best achieved by introducing the metal co-activators and thiol activators to the reaction site at a time interval and frequency sufficient to maintain the isomerase at or near its optimum activity level. For continuous reactions, it is advantageous to continuously introduce the iron ions (desirably with another co-metal) into the feed stream with at least periodic additions of the thiol activator to maintain a high level of productivity. Preferably the total activator combination (e.g., magnesium ions, iron ions and thiol activator) are continuously admitted to the influent feed stream or isomerization media.

Fructose syrup manufacturers conventionally obtain isomerases from the isomerase producer in a dry form. It is advantageous to rehydrate these dry isomerases with a pretreating solution comprised of the thiol activator and iron ions (preferably including other desired co-metal activators) as taught in my parent application Ser. No 560,658 entitled "Dry Isomerase Activation," filed Mar. 20, 1975 and further illustrated in the following examples. This pretreatment method saturates and rehydrates the isomerase with the activating system. The resultant iron-isomerase complex or other co-metal factors are thus converted to a high activity level with the necessary stabilizing iron ions. The pretreatment method equilibrates and loads the isomerase with the complexing metal activators for most effective stabilization and isomerization of the dextrose to fructose.

The activating systems disclosed herein apply to batch and continuous processes (including multiple staged or recycling operations). As recognized by the art, the optimum operative temperature, pH and other isomerization conditions for maximum fructose productivity and half-life depend upon the character and type of glucose isomerase which is used in the isomerization. As a general rule, the iron-thiol activator system (with or without co-metal activators) will not significantly alter these operative conditions. Illustrative pH conditions herein generally range from about 6.0 to about 8.5 and preferably from about pH 7.0 to about pH 8.0. Likewise, isomerization temperatures of about 50° to about 80° C (preferably between about 55° to about 70° C.) may be used to isomerize the dextrose to fructose. Initial dextrose feed syrup solids (advantageously containing at least 93% dextrose and preferably at least 95% dextrose on a d.s.b.) between about 25% to about 75% dry substance solids and preferably from about 30% to about 55% may be used. The isomerization is typically conducted for a period of time and under conditions sufficient to isomerize at least 25% of the dextrose to fructose (preferably at least 42% fructose). Conventional additives known to shift the dextrose-fructose enzymatic equilibrium point to higher fructose yields may be conjointly used with the present activating system.

Conventional buffers, antioxidants, preservatives and other isomerase co-factors (e.g., arsenates, borates, etc.) may be added as desired or required in the isomerization reaction. Co-metal activator salts which either contain more than one metal activator or metal activator and thiol activator combinations may be used to fulfill a multiplicity of activating functions. Reagents which provide sulfite ions are especially useful since they function as preservatives and buffers as well as coactivating factors for the glucose isomerase in the isomerization reaction. Due to the isomerization conditions frequently used to produce dextrose syrups and frequent presence in water supplies of heavy metal contaminants which deactivate or poison isomerases, anions which function as scavengers or complexing reagents for these heavy metal contaminants may be effectively used with the activator systems of this invention. For example, oxalate salts (e.g., sodium, ammonium, magnesium, potassium ferrous oxalates, etc.) will effectively precipitate these heavy metals, to provide about a 5% to 10% increase in fructose productivity and isomerase activity.

The following examples are illustrative of the invention.

EXAMPLE I

An immobilized, dry isomerase preparation (41.3 grams) obtained from Bacillus coagulans and immobilized in accordance with the teachings of West German Patent Specification No. 2,345,185 by Novo Terapeutisk Laboratorium and identified as Novo SP 113 A (sold and distributed by Novo Industrie, Copenhagen) was pretreated by uniformly admixing and slurrying the dry isomerase initially with 75 ml. glucose syrup (50% dry solids of which 94% was glucose) followed by the admixing thereto of a 5 ml. solution containing 1M sodium sulfite (1.3% of the enzyme dry weight) and 2.1 grams ferrous sulfate (Melanterite-a 0.1M $Fe^{++}$) and 5 ml. aqueous solution of 1M $Mg^{++}$ ion (magnesium sulfate). The slurry was mixed for 30 minutes at 23° C. and charged to an isomerization reactor (three-necked flask) containing 1 liter of a 55° C. glucose syrup (at 94% glucose and 50% d.s.b.) which contained 0.005M $Mg^{++}$ ion (magnesium sulfate), 0.005M sodium sulfite and 20 ppm $Fe^{++}$ ion (0.00036M ferrous sulfate). The contents of the isomerization reaction were gently stirred and maintained for 6.5 hours at 55° C. and pH 7.0. Thereafter fresh glucose syrup which contained 0.005M $Na_2SO_3$, 0.005M $Mg^{++}$ ion and 0.00036M ferrous ion at a rate of 1 liter per day was continuously charged to the reactor with a corresponding rate withdrawal of isomerized syrup therefrom. The reactor was continuously run for 13 days.

The total amount of fructose produced by the isomerization reaction was determined by high pressure liquid chromatographic analysis for each 24 hour period with the isomerase activity (in International Glucose Isomerase Units per gram) for each 24 hour period being calculated by the following equation:

$$\frac{IGIU}{gm} = \frac{(\frac{\text{grams fructose}}{\text{day}})(3.86)}{\text{isomerase weight} \frac{(50 - \% \text{ fructose})}{(50)}}$$

Fructose productivity (in grams) for each of the 13 days was: 1 (day) - 180 grams and 106 IGIU of isomerase; 2 - 223 grams and 110 IGIU/gm of isomerase; 3 - 231 grams and 105 IGIU/gm of isomerase; 4 - 226 grams and 96 IGIU/gm of isomerase; 5 - 202 grams and 84 IGIU/gm of isomerase; 6 - 209 grams and 85 IGIU/gm of isomerase; 7 - 215 grams and 85 IGIU/gm of isomerase; 8 - 206 grams and 69 IGIU/gm of isomerase; 9 - 200 grams and 63 IGIU/gm of isomerase; 10 - 195 grams and 56 IGIU/gm of isomerase; 11 - 201 grams and 63 IGIU/gm of ismerase; 12 - 173 grams and 45 IGIU/gm of isomerase; and 13th day 175 grams and 48 IGIU/gm of isomerase.

The calculated glucose isomerase units/gram isomerase for each day were then plotted on semi-logarithmic graph paper (IGIU on Y axis and days on X axis) and the isomerase half-life was determined by drawing a line through the above recorded points and recording the points of time at which the glucose isomerase had one-half of its initial activity. Initial isomerase activity was 142 IGIU/gm isomerase with an isomerase half-life of about 8 days.

For comparative purposes, this example was repeated eliminating the ferrous ion and sodium sulfite from the pretreament solution and the isomerization reaction (i.e., relying upon $Mg^{++}$ as the isomerase activator). Initial glucose isomerase activity for the $Mg^{++}$ activated system without the cooperative effect was 105 IGIU/gm glucose isomerase and a half-life of 4.7 days which illustrates the $Fe^{++}$ and thiol activators enhanced isomerase activity by 135% and half-life by 170%.

EXAMPLE II

The effectiveness of thiol activators and iron ions (including supplemental or other added metal activator combinations thereof) was studied and compared with conventional and known activator systems. Each assay run was conducted with a one gram dry sample of glucose isomerase (*Bacillus coagulans* source) immobilized in accordance with the teachings of West German Patent Specification No. 2,345,185 by Novo Industri, Copenhagen.

In each run, a one gram sample of the dry immobilized isomerase was initially pretreated (to hydrate, saturate and activate the dry isomerase) for 30 minutes at 23° C. with an activating stock solution comprised of 10 ml. of aqueous buffered dextrose solution (6 grams dextrose - 0.2M sodium maleate buffered at pH 7.0). To study the effect of different activator combinations upon isomerase activity, different activators at varying concentrations were added to the aforementioned stock solution. The activators and concentrations (in moles) added to the stock solution and used to pretreat the isomerase in each of the runs are recorded in Tables 1 and 2.

The total pretreatment solution-slurry (including the hydrated, activated isomerase and the 10 ml. activating solution) for each run was then used in an isomerization assay test to determine the efficacy of the different activator systems. In each assay test, the total pretreatment solution-slurry was diluted to 50 ml. (40 ml. of deionized water containing 24 grams of pure anhydrous glucose and 0.2M sodium maleate, adjusted to pH 7.0 with 10% sodium hydroxide or dilute aqueous hydrochloric acid) along with designated activators to provide an isomerization assay media for each run which contained the activator and concentration levels as reported in Tables 1 and 2. As in Example I, the sulfate salts of magnesium, ferrous and cobalt were used as activator ion source materials. The glucose isomerization reaction for each assay test was conducted for one hour at 65° C. in a shaker water bath with 50 ml. of the assay substrate (125 ml. Erlenmeyer flasks). After one hour, the isomerization reaction was immediately terminated in each run by the addition of 5 ml. of glacial acetic acid. Fructose yields were determined by optical rotation in a 2d tube. The isomerase activity assay results for the comparative runs are tabulated in Tables 1 and 2.

The Table 1 and Table 2 results show that iron is relatively ineffective as a conventional activator when used by itself, but is significantly more effective when used in conjunction with a thiol activator and even more effective when further used in conjunction with $Mg^{++}$.

iron ion concentration will result in a corresponding increase in glucose isomerase activity. In a batch operation, the total amount of iron ion available to complex with the isomerase is limited by the amount of iron ion in the batch. In a continuous operation, a larger volume of syrup is used and thus more iron ions would be made available to the isomerase even though an equivalent $Fe^{++}$ molarity were used as a feed syrup. Test 9 illustrates sufficient iron ion in combination with $Mg^{++}$ and

TABLE I

| ASSAY TEST NO. | NOVO ISOMERASE | PRETREATMENT SOLUTION (Activators - Concentration) | | | | | ISOMERIZATION ASSAY MEDIA (Activators - Concentration) | | | | | GLUCOSE ISOMERASE ACTIVITY IGIU/GM ISOMERASE |
|---|---|---|---|---|---|---|---|---|---|---|---|---|
| | | $Co^{++}$ (M) | $Mg^{++}$ (M) | $Na_2SO_3$ (M) | KCSN (M) | $Fe^{++}$ (M) | $Co^{++}$ (M) | $Mg^{++}$ (M) | $Na_2SO_3$ (M) | KSCN (M) | $Fe^{++}$ (M) | |
| 1 | SP113A | — | 0.10 | 0.025 | — | — | — | 0.02 | 0.005 | — | — | 298 |
| 2 | " | — | 0.10 | — | — | — | — | 0.02 | — | — | — | 298 |
| 3 | " | 0.005 | 0.10 | 0.025 | — | — | 0.001 | 0.02 | 0.005 | — | — | 588 |
| 4 | " | 0.005 | 0.10 | 0.05 | — | — | 0.001 | 0.02 | 0.010 | — | — | 626 |
| 5 | " | — | 0.10 | 0.05 | — | 0.018 | — | 0.02 | 0.010 | — | 0.0036 | 424 |
| 6 | " | — | 0.10 | 0.10 | — | 0.018 | — | 0.02 | 0.020 | — | 0.0036 | 424 |
| 7 | " | — | 0.10 | 0.05 | — | 0.001 | — | 0.02 | 0.010 | — | 0.0002 | 166 |
| 8 | " | — | 0.10 | 0.05 | — | 0.005 | — | 0.02 | 0.010 | — | 0.001 | 202 |
| 9 | " | — | 0.10 | 0.05 | — | 0.01 | — | 0.02 | 0.010 | — | 0.002 | 375 |
| 10 | " | — | — | 0.05 | — | 0.01 | — | — | 0.010 | — | 0.002 | 280 |
| 11 | " | — | 0.01 | 0.05 | — | 0.02 | — | 0.002 | 0.01 | — | 0.004 | 420 |
| 12 | " | — | — | 0.10 | — | 0.02 | — | — | 0.02 | — | 0.004 | 360 |
| 13 | SP113E | 0.01 | 0.01 | 0.10 | — | — | 0.002 | 0.002 | 0.02 | — | — | 307 |
| 14 | " | 0.01 | 0.10 | — | 0.01 | — | 0.002 | 0.02 | — | 0.002 | — | 308 |
| 15 | " | 0.006 | 0.10 | 0.025 | — | — | 0.0012 | 0.02 | 0.005 | — | — | 289 |
| 16 | SWEET-ZYME - S | — | 0.10 | — | 0.025 | 0.01 | — | 0.02 | — | 0.005 | 0.002 | 413 |
| 17 | " | 0.001 | 0.10 | 0.05 | — | — | 0.002 | 0.02 | 0.01 | — | — | 555 |
| 18 | SP113E | 0.12 | 0.2 | 0.05 | — | — | 0.012 | 0.02 | 0.005 | — | — | 289 |
| 19 | " | 0.12 | 0.2 | — | 0.003 | — | 0.012 | 0.02 | — | 0.003 | — | 279 |
| 20 | " | — | 0.2 | 0.05 | 0.003 | 0.0012 | — | 0.02 | 0.005 | 0.003 | 0.0012 | 249 |
| 21 | " | — | 0.2 | 0.10 | 0.005 | 0.02 | — | 0.02 | 0.01 | 0.005 | 0.002 | 276 |
| 22 | " | — | 0.2 | 0.2 | — | 0.02 | — | 0.02 | 0.020 | — | 0.002 | 264 |
| 23 | " | — | 0.2 | 0.05 | — | 0.02 | — | 0.02 | 0.005 | — | 0.002 | 255 |
| 24 | " | — | 0.2 | — | — | 0.02 | — | 0.02 | — | — | 0.002 | 229 |
| 25 | SWEET-ZYME - S | 0.02 | 0.02 | 0.10 | — | — | 0.002 | 0.002 | 0.01 | — | — | 555 |
| 26 | " | — | 0.05 | — | — | — | — | 0.005 | — | — | — | 348 |
| 27 | " | 0.008 | 0.02 | — | — | — | 0.0008 | 0.002 | — | — | — | 419 |
| 28 | " | — | 0.05 | — | 0.05 | 0.02 | — | 0.005 | — | 0.005 | 0.002 | 413 |
| 29 | " | — | 0.05 | — | 0.05 | 0.002 | — | 0.005 | — | — | 0.0002 | 346 |
| 30 | " | — | 0.05 | — | — | — | — | 0.01 | — | — | — | 152 |

TABLE 2

| Assay Test No. | NOVO ISOMERASE | PRETREATMENT SOLUTION (Activators Concentration) | | | | | ISOMERIZATION ASSAY MEDIA (Activators Concentration) | | | | | GLUCOSE ISOMERASE ACTIVITY IGIU/GM ISOMERASE |
|---|---|---|---|---|---|---|---|---|---|---|---|---|
| | | $Co^{++}$ (M) | $Mg^{++}$ (M) | $Na_2SO_3$ (M) | KCSN (M) | $Fe^{++}$ (M) | $Co^{++}$ (M) | $Mg^{++}$ (M) | $NaSO_3$ (M) | Sodium Oxalate (M) | $Fe^{++}$ (M) | |
| 31 | SWEET-ZYME - S | 0.005 | 0.05 | — | — | — | 0.001 | 0.01 | — | — | — | 391 |
| 32 | " | 0.005 | 0.05 | 0.05 | — | — | 0.001 | 0.01 | 0.01 | — | — | 411 |
| 33 | " | — | 0.05 | 0.05 | — | 0.005 | — | 0.01 | 0.01 | — | 0.001 | 330 |
| 34 | " | — | 0.04 | — | — | 0.004 | — | 0.008 | — | — | 0.0008 | 227 |
| 35 | " | — | 0.04 | 0.04 | — | 0.004 | — | 0.008 | 0.008 | 0.008 | 0.008 | 342 |

The SP113A, SP113E and SWEETZYME samples differed in potency. Accordingly, assay tests 1–12 are representative of the results and observed differences obtained with the SP113A isomerase; tests 13–15 and 18–24 for SP113E; and 16–17 and 25–35 for "SWEETZYME".

As illustrated by tests 1 and 2, magnesium ions without any other metal activator had a glucose isomerase activity of 298 IGIU/gram without any measurable difference when a thiol activator is added to assay subtrate. The $Co^{++}$ and $Mg^{++}$ (3) combination provided 588 IGIU/gm and the sulfite ion addition thereto (i.e., 4) increased this activity to 626 IGIU/gm. The 424 IGIU/gm results for tests 5 and 6 are significantly higher than the 298 results of tests 1 and 2 and illustrates the effectiveness of the thiol and iron activator system. Tests 7 and 8 both contain $Mg^{++}$, $Fe^{++}$ and $SO_3^=$ ions and provided lower assay results than tests 1 and 2. It will be observed from the Tables, that an increase in the $SO_3^=$ to form a viable isomerase complex (i.e., 375 IGIU/gm). Run 12 illustrates a high glucose isomerase activity of 360 IGIU/gm (without any other metal activator such as $Co^{++}$ or $Mg^{++}$) by using a sufficient amount of iron ion and thiol activator to provide a significantly more viable isomerase (notwithstanding the absence of another co-metal activator) than is achieved with $Mg^{++}$ alone. Further improvements which may be achieved by the $Mg^{++}$-$Fe^{++}$-$SO_3^=$ system are shown by test 11 (i.e., 420 IGIU/gm) which is significantly superior to that of tests 1 and 2.

Tests 13–15 and 18–24 were conducted on SP113A isomerase. Tests 13–15 and 18–19 illustrate the effectiveness of the $Mg^{++}$ and $Co^{++}$ activator system while test 24 shows the ineffectiveness of $Mg^{++}$ without $Co^{++}$. The improved efficacy of the thiol activator and an iron ion activator system over the $Mg^{++}$ and $Fe^{++}$ system without the thiol activator (e.g., see test 24) is shown by tests 20–23.

Similar differences are evident by a comparison of the 16–17 and 25–35 assay test results, with $Mg^{++}$ by itself at 152 IGIU/gm for No. 30 $Fe^{++}$ and $Mg^{++}$ (No 34), assaying at 227 IGIU/gm and $Mg^{++}$ by itself (348 IGIU) for No. 26 (compared with No. 34) and the more viable $Fe^{++}$ – $Mg^{++}$ thiol activator system as illustrated by assay tests 16, 28–29, 32–33 and 35. As shown by test 35, the heavy metal scavenger effect of oxalates will further improve the effectiveness of the $Mg^{++}$—$Fe^{++}$-thiol activator system.

As previously pointed out, a relationship exists between the amount of iron ion necessary to load a glucose isomerase to an activity greater than achieved with magnesium alone or in combination with the iron ion without added thiol activator. As recognized by the art, glucose isomerases vary in total IGIU/gm isomerase. On a $10^5$ IGIU basis (via the assay method of Assay Test No. 4), it has been observed that 1 gram $Fe^{++}$ ion will typically provide a measurable increase in isomerase activity, further improvements being respectively observed at more than 0.25 and 0.5 grams $Fe^{++}/10^5$ IGIU with amounts of about 0.5 to about 2.0 $Fe^{++}$ grams/$10^5$ IGIU (preferably at least 1.0 gram) being best suited to achieve maximum activation.

The various features of the invention which are believed to be new are set forth in the following claims.

What is claimed is:

1. In a method for isomerizing dextrose to fructose with a glucose isomerase in the presence of metal ion activator or co-metal ion activator combinations wherein the metal activator or co-metal ion activators are used to stabilize and activate the glucose isomerase during the isomerizaton of dextrose to fructose in a glucose isomerization reaction, the improvement which comprises isomerizing dextrose to fructose with glucose isomerase by adding to the isomerization reaction a stabilizing and activating amount of water-soluble iron ions and water-soluble thiol activator ions.

2. The method according to claim 1 wherein the glucose isomerase is activated and stabilized with the iron ions, the water-soluble thiol activator ions and at least one other metal activator for said isomerase selected from the group consisting of manganese ions, cobalt ions and magnesium ions.

3. The method according to claim 2 wherein the iron ion concentration is greater than $5 \times 10^{-5}M$ and the thiol activator concentration is at least 0.0001M.

4. The method according to claim 3 wherein the glucose isomerase is characterized as having a greater capacity to isomerize dextrose to fructose in the presence of magnesium ions and cobaltous ions than with magnesium ions alone.

5. The method according to claim 2 wherein the glucose isomerase is characterized as having a higher glucose isomerase activity when the glucose isomerization reaction is conducted in the presence of magnesium ions and cobaltous ions than with magnesium ions alone, and a sufficient amount of iron ions and thiol activator is supplied to the glucose isomerase during the isomerizaton reaction to provide a higher glucose isomerase activity than that which is obtained when magnesium is used as the sole metal activator for said glucose isomerase.

6. The method according to claim 3 wherein in addition to the iron ion and thiol activator, the isomerization reaction is conducted in the presence of magnesium ions in an amount sufficient to measurably increase the isomerization of dextrose to fructose with said glucose isomerase.

7. The method according to claim 6 wherein the thiol activator comprises at least one member selected from the group consisting of sulfite ions, ascorbic acid ions, isoascorbic ions, thiocyanate ions and thioglycollate ions.

8. The method according to claim 7 wherein the glucose isomerase is characterized as having a greater capacity to convert dextrose to fructose when the isomerization reaction is conducted in the presence of catalytic amounts of cobaltous and magnesium ions in comparison to an isomerization reaction which is conducted with a catalytic amount of magnesium ions as the sole metal activator.

9. The method according to claim 8 wherein the thiol activator comprises an effective catalytic amount of a sulfite ion and the glucose isomerase is derived from organisms belonging to the Streptomyces genus.

10. The method according to the claim 8 wherein the thiol activator comprises an effective catalytic amount of a sulfite ion and the glucose isomerase is derived from an organism belonging to the Bacillus genus.

11. The method according to claim 9 wherein the glucose isomerase is obtained from *Bacillus coagulans*.

12. The method according to claim 2 wherein the glucose isomerase is characterized as having a higher glucose isomerase activity when the isomerization reaction is conducted in the presence of catalytic amounts of magnesium ions and cobaltous ions than with a catalytic amount of magnesium ion alone, and the isomerization reaction is conducted in the presence of from about 0.002M to about 0.02M $Mg^{++}$ ions, from about 0.00002M to about 0.03M iron ions and from about 0.0003M to about 0.1M thiol activator ions.

13. The method according to claim 12 wherein the thiol activator comprises sulfite ions and the glucose isomerase comprises a glucose isomerase derived from at least one organism selected from the group consisting of the Streptomyces genus and Bacillus genus.

14. The method according to claim 13 wherein a glucose feed syrup substantially free from cobaltous ions and containing iron ions, magnesium ions and sulfite ions is used to provide said activating ions to the glucose isomerase during the isomerization reaction.

15. The method according to claim 14 wherein the glucose isomerase is derived from *Bacillus coagulans*.

16. The method according to claim 2 wherein a dry immobilized glucose isomerase is used as a glucose isomerase source for the isomerization reaction and the dry immobilized isomerase is converted to hydrated isomerase with an aqueous activating solution contaning dextrose, thiol activator in an amount sufficient to activate and stabilize the glucose isomerase, and iron ions at a molarity substantially greater than the iron activator required to provide optimum fructose yields in a glucose isomerization with said glucose isomerase and said iron, continuing the hydration of said isomerase in said aqueous activating solution for a period of time sufficient to permit the isomerase to imbibe the aqueous activating solution and to saturate the isomerase with said activating solution and thereby increase the isomerization activity of said isomerase when said isomerase is used in the glucose isomerization reaction.

* * * * *

UNITED STATES PATENT AND TRADEMARK OFFICE
CERTIFICATE OF CORRECTION

PATENT NO. : 4,113,565
DATED : September 12, 1978
INVENTOR(S) : Thomas L. Hurst

It is certified that error appears in the above-identified patent and that said Letters Patent are hereby corrected as shown below:

Column 1, bridging lines 27 and 28; for "normaly" read ---normally---
Column 1, line 30; for "ismerization" read ---isomerization---
Column 1, line 65; for "hydroscopicus" read ---hygroscopicus---
Column 2, line 54; for "has" read ---have---
Column 2, line 63; for "has reported" read ---has been reported---
Column 4, line 31; for "know" read ---known---
Column 7, line 65; for "reconfiguratons" read ---reconfigurations---
Column 10, line 1; for "ismerase" read ---isomerase---
Column 11, Table 2 (second appearance in heading) for; $NaSO_3$" read ---$NA_2SO_3$---
Column 14, bridging lines 55 and 56; for "contaning" read ---containing---
Column 14, line 58; for "activator required" read ---activator molarity required---

Signed and Sealed this

Eighth Day of May 1979

[SEAL]

Attest:

RUTH C. MASON
Attesting Officer

DONALD W. BANNER
Commissioner of Patents and Trademarks